United States Patent
Zhou et al.

(10) Patent No.: US 12,209,274 B2
(45) Date of Patent: Jan. 28, 2025

(54) OLIGONUCLEOTIDE PROBE ARRAY WITH ELECTRONIC DETECTION SYSTEM

(71) Applicant: CENTRILLION TECHNOLOGY HOLDINGS CORPORATION, Grand Cayman (KY)

(72) Inventors: Wei Zhou, Saratoga, CA (US); Glenn McGall, Palo Alto, CA (US); Rui Mei, Palo Alto, CA (US); Filip Crnogorac, Redwood City, CA (US)

(73) Assignee: CENTRILLION TECHNOLOGY HOLDINGS CORPORATION, Grand Cayman (KY)

( * ) Notice: Subject to any disclaimer, the term of this patent is extended or adjusted under 35 U.S.C. 154(b) by 429 days.

(21) Appl. No.: 16/499,970

(22) PCT Filed: May 31, 2018

(86) PCT No.: PCT/US2018/035282
§ 371 (c)(1),
(2) Date: Oct. 1, 2019

(87) PCT Pub. No.: WO2018/222800
PCT Pub. Date: Dec. 6, 2018

(65) Prior Publication Data
US 2020/0362397 A1 Nov. 19, 2020

Related U.S. Application Data

(60) Provisional application No. 62/512,855, filed on May 31, 2017.

(51) Int. Cl.
*C12Q 1/6825* (2018.01)
*C12Q 1/6806* (2018.01)

(52) U.S. Cl.
CPC ......... *C12Q 1/6825* (2013.01); *C12Q 1/6806* (2013.01)

(58) Field of Classification Search
CPC ............... C12Q 1/6825; C12Q 1/6806; C12Q 2537/143; C12Q 2525/191; C12Q 2563/159
See application file for complete search history.

(56) References Cited

U.S. PATENT DOCUMENTS

| | | | |
|---|---|---|---|
| 8,586,385 B2 | 11/2013 | Su et al. | |
| 2004/0014086 A1* | 1/2004 | Stamatoyannapoulos | C12Q 1/6837 435/6.12 |
| 2008/0160634 A1 | 7/2008 | Su et al. | |
| 2010/0137143 A1* | 6/2010 | Rothberg | C12Q 1/6869 506/38 |
| 2012/0083417 A1 | 4/2012 | Zhou et al. | |
| 2015/0099672 A1* | 4/2015 | Berka | B01L 3/502715 506/26 |
| 2016/0060621 A1* | 3/2016 | Agresti | C12Q 1/6853 506/4 |
| 2016/0281149 A1 | 9/2016 | Hassibi et al. | |
| 2016/0362748 A1* | 12/2016 | Mongan | C12Q 1/6869 |

FOREIGN PATENT DOCUMENTS

| | | | |
|---|---|---|---|
| WO | WO-0107665 A3 * | 2/2001 | ............. B82Y 15/00 |
| WO | WO 2002044412 A1 | 6/2002 | |

OTHER PUBLICATIONS

International Search Report and Written Opinion in Corresponding PCT Application No. PCT/US2018/035282 issued Aug. 24, 2018.

* cited by examiner

Primary Examiner — Narayan K Bhat
(74) Attorney, Agent, or Firm — JONES DAY

(57) ABSTRACT

The present disclosure provides methods, device, and system for a hybridization assay to detect nucleic acid targets. The assay may use a probe array format with addressable microwells. Each microwell may retain a plurality of copies of one probe which may be complementary to a portion of a specific nucleic acid target. The plurality of copies of probes may be produced from a pooled library of probe sequences by amplification techniques, including, rolling circle amplification and emulsion-PCR. Detection of hybridization may rely on methods using ion-sensitive field effect transistor (ISFET) and optical detectors to detect signals indicating the presence of the nucleic acid targets.

18 Claims, 5 Drawing Sheets

OLIGONUCLEOTIDE PROBE ARRAY WITH ELECTRONIC DETECTION SYSTEM

CROSS-REFERENCE

This application claims the benefit of U.S. Provisional Patent Application No. 62/512,855, filed on May 31, 2017, which is entirely incorporated herein by reference.

BACKGROUND

The detection of distinctive nucleic acid sequences in a biological sample may be critical in many areas, including identifying microorganisms, diagnosing infectious diseases, detecting genetic abnormalities, identifying biomarker associated with various cancers, rating genetic susceptibility to selected diseases, and evaluating patient's response to medical treatments. One common technique for detecting distinctive nucleic acid sequences may be nucleic acid hybridization.

Nucleic acid hybridization may be a molecular biology technique, in which single-stranded deoxyribonucleic acid (DNA) or ribonucleic acid (RNA) molecules anneal to complementary DNA or RNA sequences. In particular, this technique may measure the degree of sequence similarity between DNA polymers (polynucleotides). The underlying principle for hybridization may be that the building blocks of the DNA polymer, i.e., nucleotides, include specific nitrogen-containing nucleobases (guanine "G," adenine "A," thymine "T," and cytosine "C"), all which may be capable of pairing up with complementary nucleobases (A with T and C with G) to form hydrogen bonds (two (2) between A-T and three (3) between C-G). As a result, two single stranded DNA moieties with complementary sequences may bind (hybridize) to each another and form DNA dimers (double stranded DNA structures).

This sequence-dependent property of hybridization may be the basis of many research and diagnostic applications via the signals generated by a labelled probe after successful hybridization between the probe and its target. Such an approach has led to DNA/RNA detection and quantification on solid phase blots, DNA/RNA cytogenetic localization on cells, detection and purification of specific DNA and comparative gene expression analysis, and other applications. Recently, principles of nucleic acid hybridization have been combined with next generation sequencing technology to create powerful new platforms for analysis with the hope to expand research tools in genomics and personalized medicine. Accordingly, new hybridization methodologies may be of interest in the biomedical field.

SUMMARY

Using methods, devices and systems provided in this disclosure, hybridization between a target nucleic acid and a plurality of copies of a probe may be detected in a single sample chamber using a probe array on a solid surface and an accompanying sensor array. The sample chamber and the accompanying sensor array may be individually addressable. In addition, the probe array may not be permanently associated with the same addressable locations on the solid surface.

An aspect of the present disclosure provides a method for assaying a presence of a target nucleic acid in a sample, comprising: (a) providing a chip comprising a sensor adjacent to a sample chamber, wherein the sample chamber is configured to retain a plurality of copies of a probe, wherein the probe selectively couples to the target nucleic acid, and wherein the sensor detects at least one signal indicative of a presence or absence of the target nucleic acid in the sample chamber; (b) providing the sample in the sample chamber under conditions that permit the probe to selectively couple to the target nucleic acid; (c) measuring the at least one signal; and (d) determining the presence or absence of the target nucleic acid in the sample, with the proviso that the plurality of copies of the probe are not attached to a surface of the sample chamber via a covalent bond.

In some embodiments of aspects provided herein, the sensor is in an array of a plurality of sensors in the chip. In addition, the sample chamber is in an array of a plurality of sample chambers in the chip. Further, each of the plurality of sample chambers is adjacent to at least one sensor of the array of the plurality of sensors. In some embodiments of aspects provided herein, the target nucleic acid is a fragment of a larger nucleic acid. In some embodiments of aspects provided herein, the probe is part of a library of a plurality of probes.

In some embodiments of aspects provided herein, the probe comprises: 1) a sequence of a nucleic acid fragment that is complementary to at least a portion of the target nucleic acid; and 2) a barcode sequence attached to a first end of the sequence of the nucleic acid fragment in 1). In some embodiments of aspects provided herein, the method further comprises prior to step (b): (a1) circularizing an adaptor-coupled probe template; and (a2) amplifying the adaptor-coupled probe template to form a linear amplified concatamer molecule comprising a plurality of copies of the probe. In some embodiments of aspects provided herein, the barcode sequence is between 3 and 30 nucleotides in length. In some embodiments of aspects provided herein, the method further comprises prior to step (b): (a1) delivering a single copy of a template of the probe or a single copy of a double-stranded nucleic acid comprising the probe into an aqueous microreactor in a water-in-oil emulsion, wherein the microreactor comprises a plurality of a primer capable of annealing to the probe, a single bead capable of binding to the template of the probe and amplifying a first copy of the probe which becomes attached to the bead, and an amplification reaction solution containing reagents sufficient to perform nucleic acid amplification; (a2) subjecting the microreactor to a nucleic acid amplification reaction under conditions that yield the first copy of the probe; (a3) repeating step (a2) multiple times; and (a4) breaking the water-in-oil emulsion and producing multiple copies of the probe attached to the bead. The microreactor may be a bead, a partition, a well, etc.

In some embodiments of aspects provided herein, the sample comprises a plurality of target nucleic acid molecules. In some embodiments of aspects provided herein, the sensor is part of an array of a plurality of sensors, wherein each of the plurality of sensors detects the presence or absence of at least one of the plurality of target nucleic acid molecules, and wherein each sensor of the array of the plurality of sensors is individually addressable. In some embodiments of aspects provided herein, each probe comprises: 1) a sequence of a nucleic acid fragment that is complementary to a portion of one of the target nucleic acid; and 2) a barcode sequence attached to a first end of the sequence of the nucleic acid fragment; and wherein the step (d) comprises: (d1) decoding the barcode sequence of the probe retained at the corresponding sample chamber associated with the individually addressable sensor.

In some embodiments of aspects provided herein, the chip comprises an additional sensor, wherein the sample comprises the target nucleic acid and an additional target nucleic acid, and wherein the additional sensor detects the additional target nucleic acid. In some embodiments of aspects provided herein, the additional sensor is adjacent to an additional sample chamber, wherein the additional sample chamber is configured to retain a plurality of copies of an additional probe, wherein the additional probe selectively couples to the additional target nucleic acid.

In some embodiments of aspects provided herein, the sensor comprises one ion-sensitive filed effect transistor (ISFET). In some embodiments of aspects provided herein, the sensor comprises one chemically-sensitive filed effect transistor (chemFET). In some embodiments of aspects provided herein, the sensor comprises one optical sensor. In some embodiments of aspects provided herein, the at least one signal comprises a change of pH.

Another aspect of the present disclosure provides a system for assaying a presence of a target nucleic acid in a sample, comprising: a chip comprising a sensor adjacent to a sample chamber, wherein the sample chamber is configured to retain the sample having the target nucleic acid and a plurality of copies of a probe, wherein the probe selectively couples to the target nucleic acid, wherein the plurality of copies of the probe are not attached to a surface of the sample chamber via a covalent bond, and wherein the sensor detects at least one signal from the sample, which at least one signal is indicative of a presence or absence of the target nucleic acid; a computer processor coupled to said chip and programmed to (i) measure the at least one signal while subjecting the chip in contact with the sample; and (ii) determine the presence or absence of the target nucleic acid in the sample.

In some embodiments of aspects provided herein, the sensor is in an array of a plurality of sensors in the chip. In addition, the sample chamber is in an array of a plurality of sample chambers in the chip. Further, each of the plurality of sample chambers is adjacent to at least one sensor of the array of the plurality of sensors, and wherein each sensor is individually addressable. In some embodiments of aspects provided herein, the computer processor is further programmed to (iii) map the array of individually addressable sensors; and (iv) when the probe contains a barcode sequence, to associate the barcode sequence with the corresponding individually addressable sensor. In some embodiments of aspects provided herein, the array of a plurality of sensors comprises at least 96 sensors.

In some embodiments of aspects provided herein, the sensor is ion-sensitive filed effect transistor (ISFET), chemically-sensitive filed effect transistor (chemFET), or optical sensor. In some embodiments of aspects provided herein, the chip comprises an additional sensor, and wherein the sample comprises an additional target nucleic acid. In some embodiments of aspects provide herein, the additional sensor detects at least one additional signal indicative of a presence or absence of said additional target nucleic acid.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
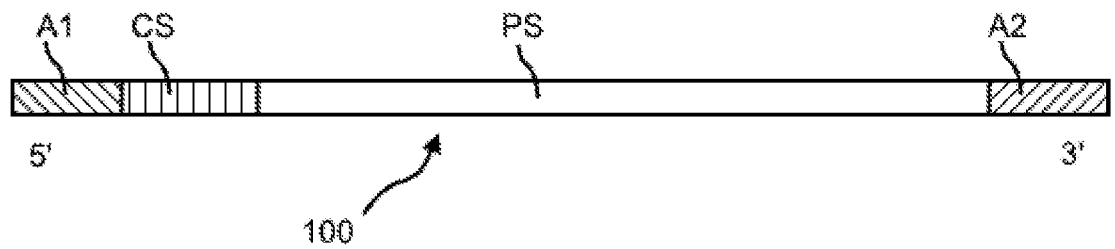
FIG. 1 illustrates an example probe 100 according to the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

Nucleotide sequence information may be used in different ways by scientists and researchers to improve humans' lives either through clinical methods or by material methods, e.g. improving crop production, creating better fuel, making a better vaccine, creating more effective pharmaceuticals, preventing disease, or preventing an outbreak of a dangerous pathogen. (See, Ansorge, W., "Next-generation DNA sequencing techniques," New Biotech., 25(4):195-203, 2009). The determination and/or detection of specific nucleotide sequences may be critical in this endeavor. Hybridization assay of nucleotide sequences may be an important tool for such research.

In many hybridization assays for nucleic acid target molecules, a probe or multiple copies of a probe may be directly attached to or bound to a surface adjacent to a detector. This may provide a one-to-one correlation between the sequence of the probe and the signals captured by the corresponding detector. In some hybridization assays, because the target nucleic acid molecules is at very low concentrations in the original sample, a nucleic acid amplification reaction may be used to yield target nucleic acid molecules in higher copy numbers and/or higher concentrations to facilitate the hybridization assay.

One type of the nucleic acid amplification may be polymerase chain reaction (PCR), which consists of repeated cycles of denaturing a template stand of DNA, annealing matched primer pairs to the DNA, and extending the DNA from the primer by a DNA polymerase. A popular PCR method used in DNA library constructions is called emulsion PCR (e-PCR) with microbeads. E-PCR method may be used by Roche's 454 (Margulies, et al., "Genome Sequencing in Microfabricated High-density Picolitre Reactors," *Nature* 437(7057):376-380, 2005) and Life Technologies' SOLiD (Valouev A et al., "A High-resolution, Mucleosome Position Map of *C. elegans* Reveals a Lack of Universal Sequence-dictated Positioning," *Genome Res.* 18(7):1051-1063, 2008) and Ion Torrent (Rothberg, et al., "An Integrated Semiconductor Device Enabling Non-optical Genome Sequencing," *Nature* 475(7356):348-352, 2011) platforms. E-PCR may require performing PCR on billions of microbeads, each isolated in its own emulsion droplet, followed by emulsion breakup, template enrichment, and bead deposition before sequencing.

Another type of the nucleic acid amplification may be rolling circle amplification (RCA) under isothermal conditions. RCA techniques may amplify a circular template nucleic acid to afford long, sometimes longer than 10 kb, single stranded linear DNA molecules that comprise concatenated copies of the template nucleic acid sequence using Phi29 DNA polymerase. (Blanco et al., "Highly Efficient DNA Synthesis by the Phage φ29 DNA Polymerase," *J. Biol. Chem.* 264, 8935, 1989; and Drmanac et al., "Human Genome Sequencing Using Unchained Base Reads on Self-Assembling DNA Nanoarrays," *Science* 327(5961):78-81, 2010). The product thus formed may include hundreds of tandem copies of the desired nucleic acid sequence to form a concatamers useful for enhancing signal strength from the ensuing hybridization reactions. Further, the concatamers may comprise internal sequences which promote the formation of secondary structures leading to compaction through intramolecular hybridization. (Drmanac et al., 2010). The resulting compact structures of nucleic acid molecules of concatamers sometimes may be referred to as "nanoballs" (NBs). A nucleic acid nanoball generally may refer to a nucleic acid particle with at least one dimension on the nanometer scale.

Large-scale multiplex analysis of multiple nucleic acid targets in a biological sample may be needed in forensic science, diagnostic and medical operations. Therefore, there may be a need for an assay device and method with better performance, for example, better signal-to-noise ratio.

When facing the problem of the low concentration of a target nucleic acid molecule in the sample, current approaches may include using PCR or other amplification techniques to make multiple copies of the target nucleic acid molecule and subjecting the amplicons to probes for detection. One benefit of this amplification-of-target approach may be the potential to allow the amplicons of the target nucleic acid molecule to have a better chance to hybridize with the probe. However, the amplification reaction may need time and special equipment to complete. The further manipulation of the sample before the hybridization assay may extend the response time of the assay. It may be better to have a hybridization assay which uses the sample directly without an amplification step for the target nucleic acid molecules.

After much effort in experimentation, Applicants have found a new device and method for hybridization assays of target nucleic acids. For example, instead of amplifying the target nucleic acid molecule, the probe may be amplified to give multiple copies, which in turn may be localized on a specific location of the assaying device so that even if the target nucleic acid molecule may exist at a low concentration in the sample, the target nucleic acid molecule may seek out and hybridize with a copy of the probe due to the sheer number of probe on that spot.

As used in this specification and the appended claims, the singular forms "a," "an" and "the" include plural referents unless the context clearly dictates otherwise. Thus, for example, reference to "a molecule" includes a plurality of such molecules, and the like.

The term "fragment" as used herein generally refers to a fraction of the original DNA sequence or RNA sequence of the particular region.

The term "target nucleic acid" as used herein generally refers to the nucleic acid fragment targeted for detection using hybridization assays of the present disclosure. Sources of target nucleic acids may be isolated from organisms, including mammals, or pathogens to be identified, including viruses and bacteria. Additionally target nucleic acids may also be from synthetic sources. Target nucleic acids may be or may not be amplified via standard replication/amplification procedures to produce nucleic acid sequences.

The term "nucleic acid sequence" or "nucleotide sequence" as used herein generally refers to nucleic acid molecules with a given sequence of nucleotides, of which it may be desired to know the presence or amount. The nucleotide sequence can comprise ribonucleic acid (RNA) or DNA, or a sequence derived from RNA or DNA. Examples of nucleotide sequences are sequences corresponding to natural or synthetic RNA or DNA including genomic DNA and messenger RNA. The length of the sequence can be any length that can be amplified into nucleic acid amplification products, or amplicons, for example up to about 20, 50, 100, 200, 300, 400, 500, 600, 700, 800, 1,000, 1,200, 1,500, 2,000, 5,000, 10,000 or more than 10,000 nucleotides in length.

The term "template" as used herein generally refers to individual polynucleotide molecules from which another nucleic acid, including a complementary nucleic acid strand, may be synthesized by a nucleic acid polymerase. In addition, the template may be one or both strands of the polynucleotides that are capable of acting as templates for template-dependent nucleic acid polymerization catalyzed by the nucleic acid polymerase. Use of this term may not be taken as limiting the scope of the present disclosure to polynucleotides which are actually used as templates in a subsequent enzyme-catalyzed polymerization reaction.

The term "analyte" as used herein generally refers to a substance to be detected or assayed by the method of the present disclosure. It is to be construed broadly as any compound, molecule, or other substance of interest to be detected, identified, or characterized. Analytes may include nucleic acid fragments including DNA, RNA or synthetic analogs thereof. Other type of analyte may be chemicals, including ions, in the sample or assay solutions, before, during or after the addition of target nucleic acid. A nucleic acid analyte may incorporate one or more reactive ligands which may serve as members of a binding pair. Such ligands are incorporated into the analyte in such a manner as to enable the ligand to react with a second member of a binding pair. Ligands may be coupled either at the 3' end, the 5' end or at any point between the 3' and 5' ends of the nucleic acid analyte. Additionally, reporter moieties may also be incorporated into the nucleic acid analyte in a manner similar to ligand incorporation. The nucleic acid analyte may be ligand-free but may also incorporate sequence segments complementary to nucleic acid fragments comprising other reagents within the assay system.

The term "ligand" as used herein generally refers to one member of a binding pair which has been incorporated into the nucleic acid analyte and may include but is not limited to antibodies, lectins, receptors, binding proteins or chemical agents.

The term "binding pair" as used herein generally refers any of the class of immune-type binding pairs, such as antigen/antibody or hapten/anti-hapten systems; and also any of the class of nonimmune-type binding pairs, such as biotin/avidin; biotin/streptavidin; folic acid/folate binding protein; complementary nucleic acid segments; protein A or G/immunoglobulins; and binding pairs which form covalent bonds, such as sulfhydryl reactive groups including maleimides and haloacetyl derivatives, and amine reactive groups such as isotriocyanates, succinimidyl esters and sulfonyl halides. (See, Bobrow, et al., "Catalyzed reporter deposition, a novel method of signal amplification. Application to immunoassays," *J. Immunol. Methods,* 125:279-85, 1989).

Specifically, for immune-type binding pairs, the antibody member, whether polyclonal, monoclonal or an immunoreactive fragment thereof, of the binding pair can be produced by various methods. The term "immunoreactive antibody fragment" or "immunoreactive fragment" as used herein generally refers to fragments which contain the binding region of the antibody. Such fragments may be Fab-type fragments which are defined as fragments devoid of the Fc portion, e.g., Fab, Fab' and F(ab')$_2$ fragments, or may be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies.

The term "reporter conjugate" as used herein generally refers to a conjugate comprising an enzyme, fluorescent molecule or radioactive label coupled to one member of a binding pair. The member of the binding pair can be an antibody, nucleic acid sequence or some immuno-reactive or affinity-reactive substance.

The term "reporter" or "reporter moiety" as used herein generally refers to any entities capable of detection via enzymatic methods or energy emission; including, but not limited to, fluorescent moieties, chemi-luminescent moieties, particles, enzymes, radioactive tags, or light emitting moieties or molecules.

The term "particle" as used herein generally refers to latex particles that are dyed, submicron and uniform, but also includes other particles that otherwise are capable of detection.

The term "conjugate" as used herein generally refers to two or more molecules (and/or materials such as nanoparticles) that are covalently linked into a larger construct. In some embodiments, a conjugate comprises one or more biomolecules (such as peptides, antibodies, nucleic acids, proteins, enzymes, sugars, polysaccharides, lipids, glycoproteins, biopolymers (e.g., PEG), and lipoproteins) covalently linked to one or more other molecules, such as one or more other biomolecules. In other embodiments, a conjugate includes one or more specific-binding molecules (such as antibodies and/or nucleic acid sequences) covalently linked to one or more detectable labels (such as fluorescent molecules, fluorescent nanoparticles, haptens, enzymes and combinations thereof).

The term "signal" as used herein generally refers to a time-varying quantity associated with one or more properties of a sample that is assayed. A signal can be continuous in the time domain or discrete in the time domain.

The term "PCR" or "Polymerase chain reaction" as used herein generally refers to the enzymatic replication of nucleic acids, which uses thermal cycling for example to denature, extend and anneal the nucleic acids.

The term "probe" or "capture probe" or "capture molecule" as used herein generally refers to a molecular species or other marker that can bind to a specific target nucleic acid sequence. A probe can be any type of molecule or particle. Probes can comprise molecules and can be bound to the substrate or other solid surface, directly or via a linker molecule. In the present disclosure, probes may not, directly or indirectly, be bound to the surface of the sample chamber through covalent bonds, as described hereinafter. However, the probes may be restricted in movement within the confines of the sample chamber the probes reside. The restriction can be caused by charge-charge interaction or magnetic interaction. When the probe is a sequence of nucleic acid, it may be a single-stranded sequence, or a double-stranded sequence comprising a single-stranded sequence of interest.

Two polynucleotides "hybridize" when they associate to form a stable duplex, e.g., under relevant assay conditions. Nucleic acids may hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York)

The term "sensor" or "detector" as used herein generally refers to a device, generally including optical, magnetic, or electronic components that can detect signals. Generally speaking, a sensor refers to a device that may be used to sense the presence of an analyte. In particular, a sensor may be an ambient sensing device such as, for example, ion sensitive and chemical sensitive devices that generate an electrical signal (e.g., current, potential, or conductivity) based on the presence of or concentration of an analyte in the sample being tested. An optical sensor may be another type of sensor.

The term "about" or "nearly" as used herein generally refers to within +/−15%, 10%, 9%, 8%, 7%, 6%, 5%, 4%, 3%, 2%, or 1% of the designated amount.

The term "label" as used herein generally refers to a specific molecular structure that can be attached to a targeted molecule, to make the target molecule distinguishable and traceable by providing a unique characteristic not intrinsic to the targeted molecule. Labels can comprise molecular structures that, once attached to a nucleic acid sequence, provide a distinct characteristic that is not inherent to those nucleic acid molecules. Examples can be labels that create unique optical characteristics. Sometimes, optical labels may be used. An optical label can be used as single signal generating entity or part of a dual-molecule reporter in the role of either an energy donor, or energy acceptor, or other methods. Acceptors and donors can both be fluorophores molecules. Whether a fluorophore is a donor or an acceptor may be based on its excitation and emission spectra, and the fluorophore with which it is paired.

In some cases, the use of incorporated non-radioactive labels for the detection of nucleic acids may be used. For example, nucleic acids modified with biotin (U.S. Pat. No. 4,687,732; European Patent No. 063879), digoxin (European Patent No. 173251) and other haptens may be used. For example, U.S. Pat. No. 5,344,757 uses a nucleic acid probe containing at least one hapten as label for hybridization with a complementary target nucleic acid bound to a solid membrane. The sensitivity and specificity of these assays may be based on the incorporation of a single label via an amplification reaction which can be detected using an antibody specific to the label. Some cases may involve an antibody conjugated to an enzyme. In some cases, the addition of a substrate can generate a calorimetric or fluorescent change which can be detected with an instrument.

The term "complementary" refers to a polynucleotide that forms a stable duplex with its "complement" under relevant assay conditions. Two polynucleotide sequences that are complementary to each other have mismatches at less than about 20% of the bases, at less than about 10% of the bases, at less than about 5% of the bases, or have no mismatches.

A "polynucleotide sequence" or "nucleotide sequence" or "a sequence of a nucleic acid" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

The term "DNA polymerase" as used herein generally refers to a cellular or viral enzyme that synthesizes DNA molecules from their nucleotide building blocks.

The term "chemically-sensitive field-effect transistor" or "chemFET" as used herein generally refers to the type of detectors irrespective of the particular chemical system such device is adapted to, or interface with. A chemFET can be a chemical sensor that is used in the detection of chemical processes of interest by detecting a threshold voltage affected by the modulation of the channel conductance of the device.

The term "ion-sensitive field effect transistor" or "ISFET" as used herein generally refers to an impedance transformation device that is configured to selectively measure ion activities in a solution (e.g., hydrogen ions in the solution). One theory of operation of an ISFET is given in "Thirty years of ISFETOLOGY: what happened in the past 30 years and what may happen in the next 30 years," Bergveld, Sens. Actuators, 88:1-20 (2003). The present disclosure is not limited to any particular class of chemFET or ISFET and the use of these terms may not be interpreted in a limiting sense.

The term "array" as used herein, when describing a device, a system, sensors, sample chambers, etc., generally refers to a one-dimensional or two-dimensional set of microstructures. An array may be any shape. For example, an array may be a series of microstructures arranged in a line, such as the array of squares. An array may be arranged in a square or rectangular grid. There may be sections of the array that are separated from other sections of the array by spaces. An array may have other shapes. For example, an array may be a series of microstructures arranged in a series of concentric circles, in a series of concentric squares, a series of concentric triangles, a series of curves, etc. The spacing between sections of an array or between microstructures in any array may be regular or may be different between particular sections or between particular pairs of microstructures. The microstructure arrays of the present disclosure may be comprised of microstructures having zero-dimensional, one-dimensional or two-dimensional shapes. The microstructures having two-dimensional shapes may have shapes such as squares, rectangles, circles, parallelograms, pentagons, hexagons, irregular shapes, etc.

Devices and Methods

The present disclosure provides methods, devices, and systems to enable multiplex detection of nucleic acid hybridization reactions. The methods, device, and systems of the present disclosure can comprise components including, but not limited to:

1. Sample chamber, which may include an aqueous environment in which a plurality of free-moving nucleic acid targets, to be analyzed, are present. There may be an array of sample chambers. Each sample chamber of the array may be at an individually addressable location on a solid surface. Each addressable location (or a "pixel") may retain a plurality of copies of a nucleic acid sequence that can specifically hybridize to a specific target. Each addressable location may not accommodate more than one nucleic acid probe, as explained hereinafter. An array of sample chambers may be an array of micro-wells on a semiconductor chip;

2. Probe array, which may comprise a plurality of nucleic acid probes. The probe array may be interfaced with the sample chamber array so that each probe corresponds to one sample chamber and, hence, becomes individually addressable. Each probe may comprise a plurality of copies of a nucleic acid sequence that can specifically hybridize to a specific target; and 3. Sensor, which may measure, in parallel, the signals generated at every pixel. Signals can be related to the labels' or reporters' presence and activity in their vicinity, as the hybridization events progress. The signals may be discrete (e.g., individually resolvable) signals.

The probe array may include independently addressable locations that each location has one or a plurality of probes. Probes at a given independently addressable location of the array may be the same as or different from probes at other independently addressable locations of the array. In some cases, probes of a group of locations of the array may be the same.

In addition, the device may comprise a computer system. Methods, devices, and systems of the present disclosure can employ variants of the above components assembled together to create a system capable of measuring nucleic acid hybridization reactions in parallel.

Targets for Assays

Genetic materials useful as targets for the present disclosure may include, but are not limited to, DNA and RNA. There may be many different types of RNA and DNA, all of which have been and continue to be the subject of great study and experimentation. Targets of DNA may include, but are not limited to, genomic DNA (gDNA), chromosomal DNA, mitochondrial DNA (mtDNA), plasmid DNA, ancient DNA (aDNA), all forms of DNA including A-DNA, B-DNA, and Z-DNA, branched DNA, and non-coding DNA. Forms of RNA that may be sequenced using the present methods and compositions include, but are not limited to, messenger RNA (mRNA), ribosomal RNA (rRNA), microRNA, small RNA, snRNA and non-coding RNA. (See, Limbach et al., "Summary: The modified nucleosides of RNA," *Nuc. Acids Res.*, 22(12):2183-2196, 1994).

Nucleotides may include, but are not limited to, the naturally occurring nucleotides G, C, A, T and U, as well as rare forms, such as, Inosine, Xanthosine, 7-methylguanosine, dihydrouridine, 5-methylcytosine, and pseudouridine, including methylated forms of G, A, T, and C, and the like. (See, for instance, Korlach et al., "Going beyond five bases in DNA sequencing," *Curr. Op. Struct. Biol.*, 22(3):251-261, 2012; and U.S. Pat. No. 5,646,269). Nucleosides may also be non-naturally occurring molecules, such as those comprising 7-deazapurine, pyrazolo[3,4-d]pyrimidine, propynyl-dN, or other analogs or derivatives. Example nucleosides include ribonucleosides, deoxyribonucleosides, dideoxyribonucleosides, carbocyclic nucleosides, and the like.

Samples

Generally, any sample containing genetic material possessing a sequence of nucleotides of interest may be amenable to the present disclosure. Samples may be obtained from eukaryotes, prokaryotes and archaea. For example, samples containing genetic material whose sequence may be determined using the present disclosure include those obtained from, for instance, bacteria, bacteriophage, virus, transposons, mammals, plants, fish, insects, etc.

Samples may be human in origin and may be obtained from any human tissue containing genetic material. Generally, the samples may be fluid samples, such as, but not limited to normal and pathologic bodily fluids and aspirates of those fluids.

Purification/Isolation of DNA Sample for Assays

To prepare a sample for determination or detection of the sequence of genetic information contained therein, one may isolate and/or purify the genetic material away from other components in the original sample. There may be methods for purifying nucleic acid material from a sample. (See, for instance, Kennedy, S., "Isolation of DNA and RNA from soil using two different methods optimized with Inhibitor Removal Technology® (IRT)," *BioTechniques*, p. 19, November 2009; Molecular Cloning—A Laboratory Manual (Fourth Edition) Green, M., and Sambrook, J., Cold Spring Harbor Laboratory Press, US, 2012; Methods and Tools in Biosciences and Medicine, Techniques in molecular systematics and evolution, DeSalle et al. Ed., 2002, Birkhäauser Verlag Basel/Switzerland; Keb-Llanes et al., *Plant Molecular Biology Reporter*, 20:299a-299e, 2002).

Fragmentation of DNA Sample to Produce Targets for Assays

Fragmentation of the polynucleotide targets in a DNA sample may be conducted prior to utilization of the various methods and devices disclosed in the present disclosure. These methods may include sonication, nebulization, hydroshearing and shearing by other mechanical methods, such as, by using beads, needle shearing, French pressure cells, and acoustic shearing, etc., restriction digest, and other enzymatic methods such as use of various combinations of nucleases (DNase, exonucleases, endonucleases, etc.), as well as transposon-based methods. (See, Knierim et al., "Systematic Comparison of Three Methods for Fragmentation of Long-Range PCR Products for Next Generation Sequencing," *PLoS One*, 6(11): e28240, 2011; Quail, M. A., "DNA: Mechanical Breakage," Nov. 15, 2010, eLS; Sambrook, J., "Fragmentation of DNA by Nebulization," Cold Spring Harb. Protoc., doi:10.1101/pdb.prot4539, 2006). Generally, the goal can be to obtain polynucleotides of a base pair (bp) size range that is amenable to the assay method chosen. For instance, the fragments may be about 50 bp, about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp or more.

In one embodiment, the fragmentation of the DNA sample may be performed by chemical, enzymatic, or physical methods. The fragmenting may be performed by enzymatic or mechanical methods. The mechanical methods may be sonication or physical shearing. The enzymatic methods may be performed by digestion with nucleases (e.g., Deoxyribonuclease I (DNase I)) or one or more restriction endonucleases. In some embodiments, the fragmentation results in ends for which the sequence may not be known.

In another embodiment, the enzymatic methods may be using DNase I. DNase I can be an enzyme that nonspecifically cleaves double-stranded DNA (dsDNA) to release 5'-phosphorylated di-, tri-, and oligonucleotide products. DNase I may have activity in buffers containing $Mn^{2+}$, $Mg^{2+}$ and $Ca^{2+}$. The purpose of the DNase I digestion step can be to fragment a large DNA genome into smaller fragments of a library. The cleavage characteristics of DNase I may result in random digestion of the substrate DNA (i.e., no sequence bias for breaking the DNA molecule) and may result in the predominance of blunt-ended dsDNA fragments when used in the presence of manganese-based buffers (Melgar and Goldthwait, "Deoxyribonucleic acid nucleases. II. The effects of metal on the mechanism of action of deoxyribonuclease I," *J. Biol. Chem.* 243(17):4409-16, 1968). The range of digestion products generated following DNase I treatment of genomic templates may depend on three factors: i) amount of enzyme used (units); ii) temperature of digestion (° C.); and iii) incubation time (minutes). The DNase I digestion may be optimized to yield genomic libraries with a size range from about 50 to about 700 bp.

In one embodiment, the DNase I may digest a large substrate DNA or whole genome DNA for about 1 or about 2 minutes to generate a population of fragmented polynucleotides. In another embodiment, the DNase I digestion may be performed at a temperature between about 10° C. to about 37° C. In yet another embodiment, the digested DNA fragments may be between 50 bp to 700 bp in length.

Furthermore, in some embodiments, the digestion of genomic DNA (gDNA) substrates with DNase I in the presence of $Mn^{2+}$ may yield fragments of DNA that are either blunt-ended or have protruding termini with one or two nucleotides in length. In one embodiment, an increased number of blunt ends may be created with Pfu DNA polymerase. Use of Pfu DNA polymerase for fragment polishing may result in the fill-in of 5' overhangs. Additionally, Pfu DNA polymerase may result in the removal of single and double nucleotide extensions to further increase the amount of blunt-ended DNA fragments available for adaptor ligation (Costa and Weiner, "Protocols for cloning and analysis of blunt-ended PCR-generated DNA fragments," *PCR Methods Appl* 3(5):S95-106, 1994; Costa et al., "Cloning and analysis of PCR-generated DNA fragments," *PCR Methods Appl* 3(6):338-45, 1994; Costa and Weiner, "Polishing with T4 or Pfu polymerase increases the efficiency of cloning of PCR products," *Nucleic Acids Res.* 22(12):2423, 1994).

Amplification of Nucleic Acid Sequences

Methods for amplifying genetic materials may include whole genome amplification (WGA). (See, for instance, Lovmar et al., "Multiple displacement amplification to create a long-lasting source of DNA for genetic studies," *Hum. Mutat.*, 27:603-614, 2006). Amplification of nucleic acid sequences may employ any of a number of PCR techniques and non-PCR techniques including, but not limited to, e-PCR, RCA, transcription mediated amplification to target both RNA and DNA for amplification, nucleic acid sequence based amplification (NASBA) for constant temperature amplification, helicase-dependent isothermal amplification, strand displacement amplification (SDA), Q-beta replicase-based methodologies, ligase chain reaction, loop-mediated isothermal amplification (LAMP), and reaction &placement chimeric (RDC).

Sample Chambers

The sample chamber can have a volume from about 10 nanoliters (nL) to about 10 milliliters (mL). In some cases, the sample chamber volume may be from about 10 nL to about 100 nL, from about 100 nL to about 200 nL, from about 200 nL to about 500 nL, from about 500 nL to about 1 microliter (µL), and from about 1 µL to 100 µL. The sample chamber volume may be at least about 10 nL, 100 nL, 1 µL, 10 µL, 100 µL, 1 mL, or 10 mL. The depth of the sample chamber may be controlled when taking into consideration 1) the dimensions of the nanoball or bead each sample chamber retains, 2) the amount of solution allowed in the sample chamber to facilitate the hybridization and washing steps, and 3) the balance between retaining the retained nanoball or bead and washing away unbound target nucleic acid after the hybridization step, etc. The depth of the sample chamber may be about 50 nm, about 100 nm, about 200 nm, about 300 nm, about 400 nm, about 500 nm, about 1000 nm or more than 1000 nm.

Sample chambers may contain an aqueous solution. The aqueous solution within the sample chamber may comprise a buffered saline-based solution, such as an aqueous solution comprising a mixture of a weak acid and its conjugate base, or vice versa. The solution may comprise a plurality of target nucleic acid sequences, herein generally referred to as "targets." A sample chambers may accommodate a plurality of copies of a probe. A sample chamber may retain a plurality of copies of one probe and may not accommodate two different probes, each of which has a plurality of copies. A sample chamber may take any 3-D shape configured to retain a plurality of one probe. For example, the volume of the chamber may be tailored when considering the average size of the plurality of the probe to be retained. Further, the design of the sample chamber may include accommodations for the associated sensor so that signals indicative of the hybridization between the probe and the target nucleic acid within the confines of the sample chamber may be detected by the associated sensor. Each sample chamber and its associated sensor may be individually addressable as a pixel.

The sample chamber may be in fluid contact with other components, including but not limited to, microfluidic channels. It may also allow the addition of other non-fluidic subject such as a bead or nanoball (NB).

Probe Array

One feature of the present disclosure can be that the device has a dynamic probe array instead of a static/immobilized probe array. Many hybridization assays may construct their assay platforms by attaching a probe or copies of the same probe on the surface of a pixel through covalent chemical bonds. The probe array thus obtained may be static or immobilized, in the sense that once the probe array is formed, the makeup of the probe array may not be changed and the probe may be permanently associated with the same physical position, a specific pixel, on the chip from one assay to the next. Accordingly, when a different probe array is needed, a new chip may have to be rebuilt and the old chip may be discarded.

In contract, the present disclosure may employ a dynamic probe array, in the sense that each probe or copies of each probe may change its physical location, a pixel, on the chip from one assay to the next, without discarding the chip from one assay to the next. Consequently, the pixel associated with the probe or a plurality of probes may not be permanently fixed and may be determined during each assay. One way of determining the pixel associated with the probe or a plurality of probes of a particular assay may be to rely on utilizing the barcode sequence attached to each probe after the probe or the plurality of the probe have been retained within a specific sample chamber. Other ways of determining the pixel associated with the probe or a plurality of probes may be possible.

In some cases, oligonucleotides may be used as probes. An "oligonucleotide" as used herein may comprise a single-stranded nucleic acid. Oligonucleotides may be from 2 to about 1000 nucleotides long, from 2 to about 500 nucleotides in length, from about 10 to about 100 nucleotides long, or from about 20 to about 50 nucleotides in length. In methods, devices, and systems of the present disclosure, probes may be attached to a solid substrate or probes may not be attached to a solid substrate. Probes may be bound to a substrate directly or via a linker. Linkers may comprise, for example, amino acids, polypeptides, nucleotides, or oligonucleotides.

The solid substrate to which the probes bound may be biological, non-biological, organic, inorganic, or a combination of any of the above. The substrate may exist as one or more particles, strands, precipitates, gels, sheets, tubing, spheres, containers, capillaries, pads, slices, films, plates, or slides, for example. But the substrate may not be the sides of the sample chamber or the surface of the sensor/detector. The solid substrate may be flat or may take on alternative surface configurations. For example, the solid substrate may contain raised or depressed regions on which synthesis or deposition takes place. In some examples, the solid substrate may be chosen to provide appropriate light-absorbing characteristics. For example, the substrate may be a polymerized Langmuir Blodgett film, functionalized glass, Si, Ge, GaAs, GaP, $SiO_2$, $SiN_4$, modified silicon, or any one of a variety of gels or polymers such as polycarbonate, (poly)tetrafluoroethylene, polystyrene, (poly)vinylidenedifluoride, or combinations thereof.

Each probe or each plurality of the probes may be retained in one addressable sample chamber, identified as or referred to as "pixel" on a chip. In some cases, a chip may comprise at least about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 pixels with retained probes. In some cases, a chip may comprise at most about 2, 3, 4, 5, 6, or 7-10, 10-50, 50-100, 100-500, 500-1,000, 1,000-5,000, 5,000-10, 000, 10,000-50,000, 50,000-100,000, 100,000-500,000, 500,000-1,000,000 or over 1,000,000 pixels with retained probes. In some cases, a chip may comprise about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 pixels with retained probes.

In some cases it may be useful to have pixels which do not retain probes. Such pixels may act as control spots in order to increase the quality of the measurement, for example, by using binding to the spot to estimate and correct for nonspecific binding of analytes. In some cases, such control spots may be used to represent background signals.

In some cases, it may be useful to have redundant pixels which have identical probe sequences to another pixel but physically may not be adjacent to or in the proximity of the other pixel. The data acquired by such probe arrays may be less susceptible to fabrication non-idealities and measurement errors.

Detectors and Detection Systems

The present disclosure provides detectors that may be used to detect signals. Such signals may be used for monitoring the progression of nucleic acid hybridization. Such detectors may be optical detectors for measuring optical signals, electrochemical detectors for measuring electrochemical signals, or electrostatic detectors for measuring charge.

Signals detected by a detector may include signals conveying information about the presence, absence, and/or quantity of the labels, including the level of activity of labels at all pixels. Signals may be optical signals, such as fluorescence or chemi-luminescence. Signals may be electrical, such as electrochemical signals, electrostatic signals, resistance, capacitance, or inductance. Signals may be processed, including normalization to a background signal.

Examples of optical detectors include but are not limited to charge-coupled device (CCDs) arrays (including cooled CCDs), complementary metal-oxide-semiconductor (CMOS) imagers, n-type metal-oxide semiconductor (NMOS), active-pixel sensors (APS), or photomultiplier tubes (PMTs). Detectors may also include wavelength-selective components such as optical filters to allow measurement of selective wavelengths. Examples of other detectors include electrodes.

The detector may sample (e.g., acquire measurements) at a rate of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 90, 120, 150, 180, 210, 240, 270, 300, 400, 500, 1000, 10,000 times per minute.

The detector may comprise a light source. The light source may be used, for example, to excite fluorescence and/or colorimetric labels. The light source may comprise at least one lamp, such as an incandescent, halogen, fluorescent, gas-discharge, arc, or light emitting diode (LED). The light source may comprise a laser. The light source may produce a specific wavelength or range or wavelengths, such as UV. The light source may comprise filters for controlling the output spectrum, wavelength, or wavelengths. The light source may comprise multiple light sources, of the same or of different types, which may be used separately or in combination.

The detector may comprise various optical elements, including but not limited to filters, lenses, collimators, mirrors, reflectors, beam splitters, and diffusers. The detector may comprise a filter or filters, including but not limited to wavelength filters (e.g., color filters, UV filters, IR filters), dichroic filters, and polarizing filters. The filters may comprise multiple filters, of the same or of different types, which may be used separately or in combination. The detector may comprise elements (e.g., signal processing unit) for removing image distortion or aberration, such as barrel or fisheye distortion, pincushion distortion, mustache distortion, monochromatic aberrations (e.g., piston, tilt, defocus, spherical aberration, coma, astigmatism, field curvature, image distortion), or chromatic aberrations (e.g., axial, longitudinal, lateral, transverse). Such elements may comprise computer systems programmed to implement instructions for partially or fully correcting image distortion. For example, Brown's distortion model or the Brown-Conrady model may be used to correct for radial distortion and tangential distortion.

In some examples, the detector may measure emitted photons coming from individual pixels. These photons may be correlated to the presence and/or activity of optical labels in that area.

In some cases, the detector may comprise an integrated biosensor array, which may be built using CMOS integrated circuit (IC) fabrication processes (Plummer, et al., "Silicon Technologies: Fundamentals, Practice, and Modeling," *Prentice Hall Electronics and VLSI Series,* 2000). In such systems, herein referred to as "CMOS biochips", the sample chamber array may be placed on top of a CMOS biochip.

Also provided herein is a detection system having at least one detector that is configured to capture, detect and/or monitor signals from the probe array. Various signals may be produced, such as optical, electrical, electrochemical, magnetic, mechanical, acoustic, or electromagnetic signals. The signals may be correlated with the presence, amount, concentration, and/or binding characteristics of one or more analytes and reagents. The signals may be reflective or indicative of the progress of one or more reactions (e.g., hybridization). The signals may be detected at a single time point or multiple time points, or in real-time.

The detection system may comprise a single detector or a plurality of detectors (e.g., an array of detector). The detector(s) may be fixed or movable. The detectors may scan the probe array such that a given detector detects signals from different addressable locations of the chip during the hybridization process. In cases where a plurality of detectors is comprised in the detection system, each detector, when detecting or measuring signals, may record the specific addressable location of the signals associated with a retained plurality of copies of a probe.

Depending upon the type of signals to be detected, various types of detectors may be used in the detection system. It may include, for example, optical detectors, electrical detectors, electrochemical detectors, or electrostatic detectors. Examples of optical detectors may include but not limited to chemFET, ISFET, charge-coupled device (CCDs) arrays (including cooled CCDs), complementary metal-oxide-semiconductor (CMOS) imagers, n-type metal-oxide semiconductor (NMOS), active-pixel sensors (APS), or photomultiplier tubes (PMTs). The detectors may also include wavelength-selective components such as optical filters to allow measurement of selective wavelengths. Examples of other detectors may include electrodes.

The detection system may comprise a light source. The light source may comprise at least one lamp, such as an incandescent, halogen, fluorescent, gas-discharge, arc, or light emitting diode (LED). The light source may comprise a laser. The light source may produce a specific wavelength or range or wavelengths, such as UV. The light source may comprise filters for controlling the output wavelength or wavelengths. The light source may comprise multiple light sources, of the same or of different types, which may be used separately or in combination.

Sensors

Various sensors may be used for the present disclosure. They may include, but are not limited to, chemFET, ISFET, electronic sensors, magnetic sensor, and optical sensors.

1. chemFET

Electrochemical detection may be attractive because it may provide high sensitivity, small dimensions, low cost, fast response, and compatibility with microfabrication technologies. These characteristics have led to the development of a variety of sensors based on amperometric, potentiometric, and impedimetric signals, and the assembly of sensors into an array format for chemical, biochemical, and cellular applications.

A variety of types of chemical sensors may be used in the detection of chemical processes. One type may be a chemically-sensitive field effect transistor (chemFET). A chemFET may include a source and a drain separated by a channel region, and a chemically sensitive area coupled to the channel region. The operation of the chemFET may be based on the modulation of channel conductance, caused by changes in charge at the sensitive area due to a chemical reaction occurring nearby. The modulation of the channel conductance may change the threshold voltage of the chemFET, which may be measured to detect and/or determine characteristics of the chemical reaction of interest.

For example, chemFETs arranged in an array format may be used to monitor biological or chemical processes. Such chemFET arrays may involve detection of analytes in solution and/or detection of a charge bound to a surface coupled to an active region of the chemFET. In some systems, analytes may be distributed among an array of confinement regions, for example, microwells, in which each of the confinement regions may be coupled to at least one chemFET.

2. ISFET

An ion-sensitive field effect transistor (ISFET) may be one type of chemFET. ISFET may include an ion-sensitive layer at the chemically sensitive area of chemFET. The presence of ions in an analyte solution may alter the surface potential at the interface between the ion-sensitive layer and the analyte solution, due to the protonation or deprotonation of surface charge groups caused by the ions present in the analyte solution. The change in surface potential at the chemically sensitive area of the ISFET may affect the threshold voltage of the device. The threshold voltage may be measured to indicate the presence and/or concentration of ions within the analyte solution. The change in the threshold voltage, or the lack thereof, may be an indication of the presence or absence of the ions.

Arrays of ISFETs may be used for monitoring chemical reactions, such as DNA sequencing reactions, based on the detection of ions present, generated, or used during the reactions. See, for example, U.S. Pat. No. 7,948,015 to Rothberg et al., which is incorporated by reference herein. More generally, large arrays of chemFETs or other types of chemical sensors may be employed to detect and measure static and/or dynamic amounts or concentrations of a variety of analytes (e.g. hydrogen ions, other ions, compounds, etc.) in a variety of processes. The processes may for example be biological or chemical reactions, cell or tissue cultures or monitoring neural activity, nucleic acid sequencing, etc.

3. Optical Sensor

In certain embodiments, fluorescent and light-scattering labels may be used to indicate successful hybridization of the probe and the target nucleic acid. Examples of suitable fluorescent labels may include, but are not limited to, fluorescein dyes such as 5-fluorescein (FITC), tetrachlorofluorescein (TET) and hexachlorofluorescein (HEX); green fluorescent proteins, particularly enhanced GFP (eGFP); rhodamine dyes such as tetramethylrhodamine (TMR), and carboxytetramethylrhodamine (TAMRA); Cy3 and Cy5; and Qdot® Nanocrystals (Quantum Dot Corp., Hayward, Calif.). Fluorescently-labeled nucleotides and custom probes are commercially available from a variety of vendors (e.g. Synthegen, Houston Tex.; Qiagen, Valencia, Calif.). Suitable light-scattering labels may include, luminescent labels, metal nanoparticles, such as gold nanoparticles (Storhoff et al, "Homogeneous detection of unamplified genomic DNA sequences based on colorimetric scatter of gold nanoparticle probes," *Nat Biotechnol.* 22:883-87, 2004), and colloidal silver plasmon-resonant particles (PRPs) (Schultz et al, "Single-target molecule detection with nonbleaching multicolor optical immunolabels," *Proc Natl Acad Sci USA* 97:996-1001, 2000).

The fluorescent label may be incorporated into the target nucleic acid prior to target/probe hybridization, or after the hybridization. The label may be directly bound to or incorporated in the target nucleic acid, or it may be attached to the target nucleic acid via a linker such as biotin-streptavidin. In one embodiment, the labels may be fluorescent, attached to the target nucleic acids through different linkers. In the detection step, the labels may be distinguished based on different optical influences on the labels by the different linkers. In a further embodiment, the labels may be fluorescent, and be attached to the target nucleic acids through different linkers. In the detection step, the labels may be distinguished based on different optical influences on the labels by the different linkers, wherein the linkers may be carbon chains with different lengths and the polarize label may have fluorescence intensity inversely related to the label's length.

To detect the fluorescence signal, the labels may be illuminated by, e.g. high intensity mercury vapor lamps, lasers, or the like. In some cases, the illumination methods may be a laser having an illumination beam at a wavelength between 488 and 550 nm. In other cases, the dye-polynucleotides may be illuminated by laser light generated by an argon ion laser, particularly the 488 and 514 nm emission lines of an argon ion laser, or an the 532 emission line of a neodymium solid-state YAG laser. Several argon ion lasers may be available commercially which radiate simultaneously at these emission lines, e.g. Cyonics, Ltd. (Sunnyvale, Calif.) Model 2001, or the like. The fluorescence may be detected by a light-sensitive detector, e.g., a photomultiplier tube, a charged coupled device, or the like.

Luminescence is the emission of light from excited electronic states of luminescent atoms or molecules, as described above. Luminescence generally refers to all kinds of light emission, except incandescence, and may include photoluminescence, chemi-luminescence, and electrochemi-luminescence, among others. In photoluminescence, including fluorescence and phosphorescence, the excited electronic state is created by the absorption of electromagnetic radiation. In chemi-luminescence, which includes bio-luminescence, the excited electronic state is created by a transfer of chemical energy. In electrochemi-luminescence, the excited electronic state is created by an electrochemical process. In the present disclosure, without limitation, photoluminescence may be used interchangeably with luminescence and fluorescence, and luminophore may be used interchangeably with fluorophore.

Here, luminescence is emitted by luminophores associated with a reporter molecule incorporated into the target nucleic acid. Luminophores may have short (0.1-10 nanosecond) or long (10 nanosecond-1+ second) luminescence lifetimes. Such luminophores may be extrinsic, such as cyanine dyes, phenanthridines (such as ethidium bromide), acridines (such as acridine orange), indoles (such as DAPI), imidazoles, psoralens, and luminescent metal-ligand and lanthanide complexes and clyptates, among others. Additional luminophores are listed in Richard P. Haugland,

*Handbook of Fluorescent Probes and Research Chemicals* (6th ed. 1996), which is incorporated herein by reference for all purposes. Extrinsic luminophores may be associated with the polynucleotides covalently or noncovalently. Luminophores may be associated covalently using various reactive groups, especially if amines or thiols are incorporated into the nucleotides during their synthesis. Luminophores may be associated noncovalently via specific binding pairs, such as avidin and biotin, protein A and immunoglobulins, and lectins and sugars (e.g., concanavalin A and glucose). Luminophores also may be associated noncovalently by intercalating into the polynucleotide or by binding to grooves in the polynucleotide.

Luminophores may be used in a variety of luminescence assays, including fluorescence polarization (FP), fluorescence resonance energy transfer (FRET), fluorescence lifetime (FLT), total internal reflection (TIR) fluorescence, fluorescence correlation spectroscopy (FCS), and fluorescence recovery after photobleaching (FRAP), as well as their phosphorescence and higher-transition analogs, among others.

Fabrication of Probe Array

A probe array can be designed and synthesized from a pooled library of synthetic oligonucleotide capture probes. As shown in FIG. 1, each copy of a capture probe 100 may comprise a 5'-terminal adaptor A1, a coding sequence CS adjacent to A1 to serve as a non-interacting probe address, a probe sequence PS complementary to a specific target nucleic acid, and a 3'-termnal adaptor A2.

To prepare a probe array, a library pool of nucleic acid template may be prepared. The nucleic acid templates that may be amplified to make a pooled library of synthetic oligonucleotide capture probes, in general may include open circular or closed circular nucleic acid template molecules. A "closed circle" can be a covalently closed circular nucleic acid molecule, e.g., a circular DNA or RNA molecule. An "open circle" can be a linear single-stranded nucleic acid molecule having a 5' phosphate group and a 3' hydroxyl group.

In one embodiment, the single stranded nucleic acid template may contain at least one copy of a specific nucleic acid template sequence. In some embodiments, the open circle may be formed in situ from a linear double-stranded nucleic acid molecule. The ends of a given open circle nucleic acid molecule may be ligated by DNA ligase. Sequences at the 5' and 3' ends of the open circle molecule may be complementary to two regions of adjacent nucleotides in a second nucleic acid molecule, e.g., an adapter region of an anchor primer (sometimes referred to as an adapter), or to two regions that are nearly adjoining in a second DNA molecule. Thus, the ends of the open-circle molecule may be ligated using DNA ligase, or extended by DNA polymerase in a gap-filling reaction. Open circles are described in detail in Lizardi, U.S. Pat. No. 5,854,033, which is incorporated herein for all purposes. An open circle may be converted to a closed circle in the presence of a DNA ligase (for DNA) or RNA ligase following, e.g., annealing of the open circle to an anchor primer.

A starting nucleic acid template library may be constructed comprising either single-stranded or double-stranded nucleic acid template molecules, provided that the nucleic acid sequence includes a region that, if present in the library, is available for annealing, or may be made available for annealing, to an anchor primer sequence. For example, when used as a template for rolling circle amplification, a region of a double-stranded template may be at least transiently single-stranded in order to act as a template for extension of the anchor primer.

Library templates may include multiple elements, including, but not limited to, one or more regions that are complementary to the anchor primer. For example, the template libraries may include a region complementary to a sequencing primer, a control nucleotide region, and an insert sequence comprised of the sequencing template to be subsequently characterized. For example, the control nucleotide region may be used to calibrate the relationship between the amount of byproduct and the number of nucleotides incorporated.

In one embodiment, an indexing oligonucleotide or barcode sequence may be attached to members of a template library to allow for subsequent correlation of a template nucleic acid and its amplified products, i.e., the probe, with a population of nucleic acids from which the template nucleic acid is derived. For example, one or more samples of a starting DNA population may be fragmented separately using methods, e.g., restriction digestion or sonication. An indexing oligonucleotide sequence specific for each sample is attached to, e.g., ligated to, the termini of members of the fragmented population. The indexing oligonucleotide may act as a region for circularization, amplification and, optionally, sequencing, which permits it to be used to index, or code, a nucleic acid so as to identify the starting sample from which it is derived. A barcode attached to the template may result in another barcode attached to the amplified probe due to the complementarity of nucleic acid stands as a result of strand replication.

Distinct template libraries made with a plurality of distinguishable indexing primers may be mixed together for subsequent reactions. Determining the sequence of the member of the library may allow for the identification of a sequence corresponding to the indexing oligonucleotide. Based on this information, the origin of any given fragment may be inferred.

The design of terminal adaptors A1 and A2 may vary according to various factors, including, e.g., the choice of amplification method to make a plurality of copies of the capture probe. The probe sequence may be tailored for each probe array so that the pooled library may selectively bind to and capture the desired target nucleic acids leading to the detection thereof.

Further, the copy number of the probe at each addressable location of the chip may be amplified to generate a sufficient number of copies of the probe in order to produce a detectable signal by the detection methods of the present disclosure. Any suitable nucleic acid amplification methods may be used.

A number of in vitro nucleic acid amplification techniques have been described. These amplification methodologies may be differentiated into those methods: (i) which require temperature cycling—polymerase chain reaction (PCR) (see e.g., Saiki, et al., Science 230: 1350-54, 1995), ligase chain reaction (see e.g., Barany, *Proc. Natl. Acad. Sci. USA* 88: 189-193, 1995; Barringer, et al., *Gene* 89: 117-122, 1990) and transcription-based amplification (see e.g., Kwoh, et al., *Proc. Natl. Acad. Sci. USA* 86: 1173-77, 1989) and (ii) isothermal amplification systems—self-sustaining, sequence replication (see e.g., Guatelli, et al., *Proc. Natl. Acad. Sci. USA* 87: 1874-78, 1990); the Qβ replicase system (see e.g., Lizardi, et al., *BioTechnology* 6: 1197-1202, 1988); strand displacement amplification (see e.g., Walker, et al., *Nucleic Acids Res.* 20(7):1691-96, 1992).

1. Rolling Circle Amplification

Rolling circle amplification may use unique DNA and RNA polymerases (Phi29, Bst, and Vent Exo-DNA polymerase for DNA, and T 7 RNA polymerase for RNA) to generate long single stranded DNA and RNA. In RCA, the polymerase may continuously add nucleotides to a primer annealed to a circular template. The end result may be a long single-stranded DNA (ssDNA) with many repeats. In one embodiment, the probe sequence or segments thereof may be used as the RCA primer. In another embodiment, the probe sequence or segments thereof may be used as a ligation template to circularize a padlock sequence that is used as the circular template for RCA. The circular DNA template for RCA may be synthesized enzymatically or chemically via the intramolecular ligation of phosphate and ribose hydroxyl end groups. For example, a circular DNA template for RCA may be constructed via template mediated enzymatic ligation using, e.g., T4 DNA ligase or template free ligation using, e.g., CIRCLIGASE™.

Figure 2:
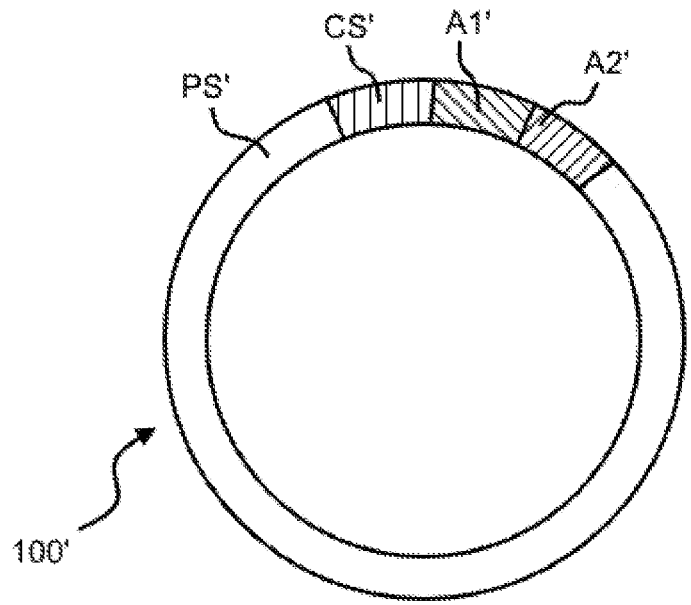
FIG. 2 illustrates a nonexclusive example of a circular DNA template 100' for the synthesis of library of probes according to the present disclosure.

If using RCA to amplify the pooled library, the templates for adaptors A1 and/or A2 may incorporate sequences required for the enablement of tandem replication of a relatively long synthetic probe sequence. Further, a helper sequence or helper sequences may comprise sequences complementary to the templates for adaptors A1 and A2 so that a linear template for the desired capture probe may circularize by base fill-in and ligation to form a single-stranded circularized template nucleic acid ("circular DNA template") for the RCA reaction. FIG. 2 shows a nonexclusive example of a circular DNA template 100'. Sequence PS' can be the template for probe sequence PS; sequence CS' can be the template for coding sequence CS, sequence A1' can be the template for adapter A1; and sequence A2' can be the template for adapter A2.

The resulting library of circular DNA templates may be amplified with Phi29 DNA polymerase via RCA reactions to form long concatamers of the capture probes in the presence of appropriate primers and amplification solutions.

The term DNA "nanoball" or "rolony" as used herein generally refers to a compacted concatamers molecule that is a result of a clonal, isothermally amplified DNA template molecule. As described above, RCA techniques may be one of the methods to amplify a circular template nucleic acid to afford long single stranded linear DNA concatamers of capture probes in the present disclosure.

In one embodiment, a linear single stranded DNA ("ssDNA"), which can be the template for a capture probe, may be modified with adaptor sequences on both the 3' and 5' ends, via ligation. The 5' end of the thus-modified template ssDNA may be further modified to include a phosphate group. In some embodiments, the adapter sequences may be specially designed to include desirable characteristics, including, but not limited to, promoting directional ligation to the ends of the template ssDNA.

After the adaptors are ligated to both ends of the template ssDNA, the linear adapted template ssDNA may be converted into a circular template ssDNA by linking the 5' and 3' ends via the CIRCLIGASE™ ligase enzyme available from Epicentre Biotechnologies (an Illumina company, Madison, Wis.).

In some cases, linear ssDNA can be circularized to provide a circular template ssDNA. For example, CIRCLIGASE™ II ssDNA Ligase can be used to circularize linear template ssDNA. This ligase is a thermostable ligase that catalyzes intramolecular ligation (i.e., circularization) of single-stranded DNA (ssDNA) substrates that have both a 5'-monophosphate and a 3'-hydroxyl group. The circularization conditions may be according to the procedures provided by the manufacturer. For example, the concentrations of the ingredients may be 0.5 pmol/µL of ssDNA, 2.5 mM MnCl$_2$, 1 M trimethylglycine (Betaine), 5 U/µL of CIRCLIGASE™ II ssDNA Ligase in a total volume of 10 µL reaction buffer of 33 mM Tris-acetate (pH 7.5), 66 mM potassium acetate, and 0.5 mM DTT. The reaction can be incubated at 60° C. for 1 h or longer. After the circularization is completed, the reaction can be incubated to 60° C. for 10 minutes to inactivate the ligase.

Then a forwarding amplification primer that is complementary to the adaptor region of the circular template ssDNA may be annealed to provide the circular template ssDNA. The annealed primer can be extended in the presence of a polymerase with high strand displacement activity, such as Phi29 DNA polymerase, to crease multiple copies of the capture probes in concatenated forms. One concatenated form of the capture probe may have about 100, about 200, about 500, and about 1000 copies or more of the probe sequence.

In some cases, the circular templates obtained above can be amplified. The amplification may be rolling circle amplification (RCA). For example, the circular template ssDNA (0.25 ng/µl) can be amplified by using Phi29 DNA polymerase (0.5 U/µl, Fermentas) for 24 h at 30° C. in a 1×Phi29 reaction buffer (33 mM Tris acetate, 10 mM magnesium acetate, 66 mM potassium acetate, 0.1% (v/v) polysorbate 20 (TWEEN®20) and 1 mM Dithiothreitol (DTT); Fermentas) containing deoxynucleotide triphosphates (dNTP) mixture (1 mM for each dNTP; Fermentas) and increasing concentration of single stranded binding protein T4 gene 32 (0-100 ng/µl, NEB).

Intramolecular hydrogen bonds or hybridization may form between regions of the adaptors which have amenable sequence for hydrogen bond formation or complementary sequence for hybridization. The probe sequence may contain regions amenable for intramolecular hydrogen bonds as well. Consequently, the linear concatamer may fold into secondary structures that condense the linear ssDNA into a three-dimensional nanoball structure that is very compact. Appropriate buffer conditions may help condense the linear ssDNA concatamers into compact nanoballs as well. Such nanoballs may have a radius of about 50 nm, about 100 nm, about 150 nm, or about 200 nm. The size of the nanoball formed may be adjusted by varying the amount of deoxynucleotide triphosphates (dNTPs) added to RCA reactions.

In one embodiment, adaptors in the linear concatamer may comprise short palindromes which promote coiling of ssDNA concatamers via reversible intramolecular hybridization into compact nanoballs.

A nanoball of a concatamer of a capture probe may hybridize with more than one copy of the desired target nucleic acid after the nanoball is retained at an addressable location on the chip and in fluidic contact with a solution containing copies of the desired target nucleic acid. Thus, the use of nanoballs of concatamers of a capture probe targeting the desired target nucleic acid may provide for signal amplification indicative of successful hybridization with the target nucleic acid.

2. Bead Emulsion PCR Amplification

In one embodiment of the present disclosure, bead emulsion amplification can be performed by attaching a nucleic acid template (e.g., DNA template) to be amplified to a solid support, for example, in the form of a generally spherical bead. The bead may be linked to a large number of a single primer that is complementary to a region of the template DNA. As a result of the amplification, the bead may be linked to many copies of the desired capture probe, which is the amplification product of the template DNA extended from the attached primers on the bead. Alternately, the bead may be linked to chemical groups (e.g., biotin) that may bind to chemical groups (e.g., streptavidin) included on the template DNA. Again, as a result of the amplification, the bead may be linked to many copies of the desired capture probe, which is amplification copy of the template DNA. The beads may be suspended in aqueous reaction mixture and then encapsulated in a water-in-oil emulsion. The template DNA may be bound to the bead prior to emulsification, or the template DNA may be included in solution in the amplification reaction mixture. In one embodiment, an amplification step may be performed prior to distribution of the nucleic acid templates to the bead emulsion PCR amplification process.

Figure 6:
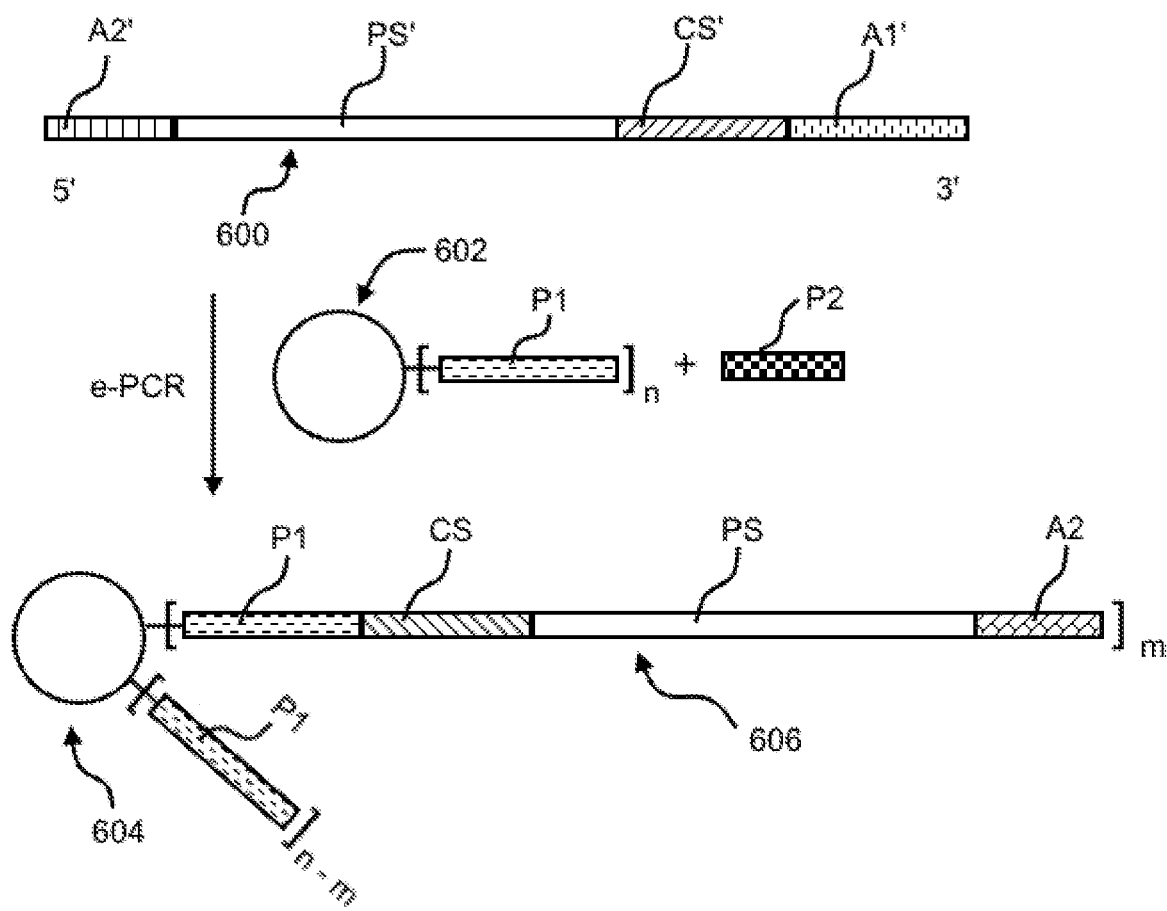
FIG. 6 shows a schematic diagram illustrating emulsion polymerase chain reaction according to the present disclosure.

One example of representative emulsion PCR (e-PCR) technique is shown in FIG. 6. Nucleic acid template 600 for e-PCR may comprise two adapters A2' and A1', a template sequence PS' for the probe sequence, and a template sequence CS' for the coding sequence. After a library of the nucleic acid templates 600 are synthesized, the e-PCR method may be employed to attach multiple copies of a probe sequence to a single bead. This may be accomplished, as shown in FIG. 6, by partition one nucleic acid template 600, a bead 602 with multiple first primer P1 attached (e.g., n primers wherein n is an integer of more than 2), a second primer P2, and other reagents (e.g., dNTPs) for PCR in the same microreactor for e-PCR (e.g., a droplet, or a microcapsule of an emulsion). At the end of the amplification which extends primer P1 according to the nucleic acid template 600, a bead 604 may be obtained, to which there may be m copies of a nucleic acid sequence 606 attached (m is an integer of more than 2 but no more than n). The nucleic acid sequence 606 may comprise the primer P1, a coding sequence CS, a probe sequence PS, and an adapter sequence A2. The probe sequence PS may be designed to be complementary to a selected target nucleic acid sequence.

In certain embodiments, the emulsion may be composed of discrete aqueous phase micro-droplets, e.g., averaging from about 60 μm to about 200 μm in diameter, enclosed by a thermostable oil phase. Each micro-droplet may contain amplification reaction solution (i.e., the reagents sufficient for nucleic acid amplification). An example of an amplification reaction solution may be a PCR reaction mixture (polymerase, salts, and dNTPs) and a pair of PCR primers. In some cases, the template DNA may be included in the reaction mixture. A subset of the micro-droplet population may include the DNA bead and the template. This subset of micro-droplet may be the basis for the emulsion PCR amplification. The remaining micro capsules may not contain template DNA and may not participate in amplification.

In one embodiment, the amplification technique used may be PCR and the PCR primers may be present in an 8:1 or 16:1 ratio (i.e., 8 or 16 of one primer to 1 of the second primer) to perform asymmetric PCR. In another embodiment, the ratio of PCR primers may be substantially equal for normal PCR. In some embodiments, thermally stable polymerase in the presence of available dNTPs may synthesize copies of an immobilized, bead bound single-stranded DNA (ssDNA) of the amplicon, which is the capture probe.

After the PCR, the emulsion may be broken and the bead with many copies of immobilized capture probe attached may be treated under conditions (NaOH, low ionic strength, or heat processing, etc.) to render the attached capture probes as ssDNA.

Sample Chambers Designs

A sample chamber may be designed to retain a plurality of copies of a probe according to the characteristics of the copies of the probe.

1. Sample Chambers for Nanoballs

Figure 3:
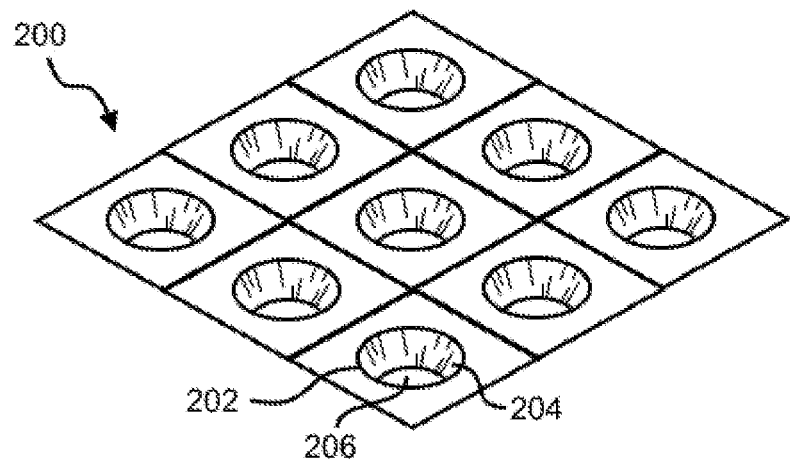
FIG. 3 shows an illustrative example of a chip 200 according to the present disclosure.
Figure 4:
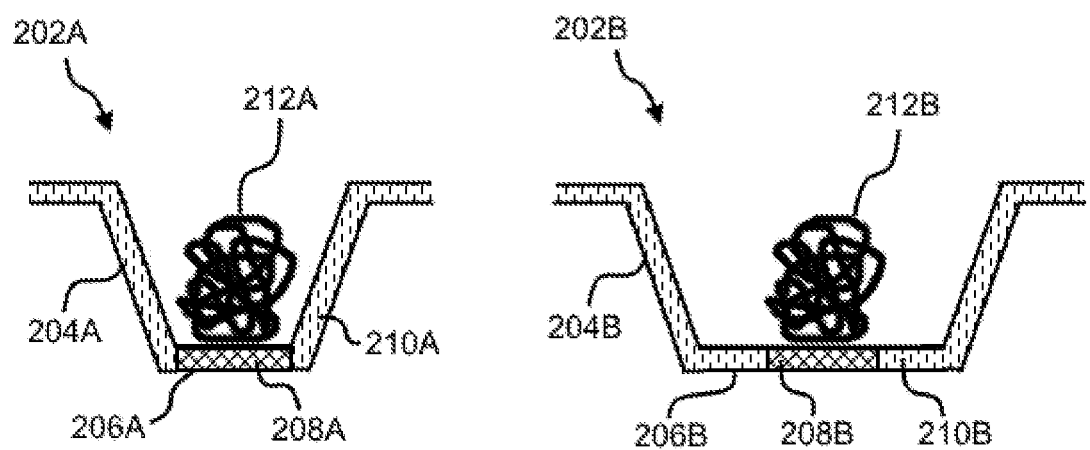
FIG. 4 depicts example sample chambers 202A and 202B according to the present disclosure.

The chip of the present disclosure can be designed to retain one nanoball within each sample chamber with an addressable location. As shown in FIG. 3, the chip 200 may comprise an array of sample chambers 202. As depicted in FIGS. 3 and 4, the shape of the sample chamber 202 may be a hollow cylinder with a circular cross section, a slanted side wall 204, and a flat surface at the bottom 206.

The distance between centers of two adjacent sample chambers may be about 700 nm, about 800 nm, about 900 nm, about 1000 nm, about 1100 nm, about 1200 nm, about 1300 nm, or from about 700 nm to about 1300 nm. The diameter of the circular bottom may be about 300 nm, about 400 nm, about 500 nm, about 600 nm, about 700 nm, about 800 nm, or from about 300 nm to about 800 nm.

Further, as shown in FIG. 4, a sample chamber 202A may have a slanted side wall 204A and a circular bottom 206A. Each circular bottom 206A may comprise a "landing site" 208A in the shape of a circle with a diameter of from about 250 nm to about 300 nm. This landing area 208A may be positively charged by chemical modifications such that it may retain a nanoball 212A of the probe with a diameter of from about 250 nm to about 300 nm via charge-charge interactions. It may be noted, other than the landing site area 208A, the rest of the surface 210A of the hollow cylinder or the top surface of the chip is not positively charged, and thereby the rest of surface of the hollow cylinder or the top surface of the chip may not form charge-charge interactions with a nanoball 212A of the probe. These surface properties of the sample chamber 202A ensure that the landing site 208A may help retain a plurality of copies of a probe in the shape of a nanoball 212A and each sample chamber 202A may retain one such nanoball 212A. The landing site may occupy the whole bottom surface of the sample chamber 202A. In another embodiment of sample chamber 202B shown in FIG. 4, the landing site 208B may occupy part of the bottom surface 206B of the sample chamber 202B to retain a nanoball 212B of the probe, while the top surface of the chip and the rest surface 210B of the hollow cylinder is not positively charged or able to retain a nanoball 212B of the probe. The landing site may comprise areas on the vertical wall of the sample chamber.

In some embodiments, a nanoball may be attached to a dendritic carrier or other types of particles, such as beads. A carrier may be porous or partially porous. If a carrier is porous or partially porous, the pore size may be of sufficient size as to permit free movement of nucleic acid (e.g., DNA), polymerase, dNTPs and other moieties useful for primer extension sequencing or other applications as appropriate.

In some embodiments, the nanoballs may be temporarily immobilized on surfaces, e.g., the surface of a sample chamber, a sensor, surface of an electrode, surface of a carrier (e.g., bead), etc. Such a surface may have any shapes, e.g., spherical, flat, rectangular, crystalline, irregular, wells, etc. In some embodiments, the substrate material of the surface, to which the nanoball attaches, may include, for example, silicon, silicon-based material, glass, modified or functionalized glass, magnetic material, plastic, metal, ceramic, gels, acrylic resins, biological material, etc. Nanoballs may be attached to a surface by any suitable method, with non-limiting examples that include nucleic acid hybridization, biotin streptavidin binding, thiol binding, photo-activated binding, covalent binding, non-covalent binding, antibody-antigen, physical confinement via hydrogels or other porous polymers, etc., or a combination thereof. In some cases, nanoballs may be digested with a nuclease (e.g., DNA nuclease) to generate smaller nanoballs or fragments from the nanoballs.

In one embodiment to prepare a slide surface to retain DNA nanoball, a layer of silicon dioxide can be grown on the surface of a standard silicon wafer (Silicon Quest International, Santa Clara, CA). A layer of titanium may be deposited over the silicon dioxide layer, and the layer of titanium may be patterned with fiducial markings with conventional photolithography and dry etching techniques. A layer of hexamethyldisilizane (HMDS) (Gelest Inc., Morrisville, PA) may be added to the substrate surface by vapor deposition, and a deep-UV, positive-tone photoresist material may be coated to the surface by centrifugal force. The resulting photoresist surface may be exposed with a selected array pattern and with a 248 nm lithography tool. The resist thus developed may produce arrays having discrete regions of exposed HMDS.

The HMDS layer in the exposed holes may be removed with a plasma-etch process, and aminosilane, for example, (3-aminopropyl)-triethoxysilane (APTES), may be vapor-deposited in the exposed holes to provide landing sites for DNA nanoballs. The resulting surface may be recoated with a layer of photoresist and cut into 75 mm×25 mm substrates, and all photoresist material may be stripped from the substrate surface with ultrasonication. Next, a mixture of about 50 µm polystyrene beads and polyurethane glue may be applied in a series of parallel lines to each diced substrate surface, and a coverslip may be pressed into the glue lines to form a muti-lane, e.g., a six-lane, gravity/capillary-driven flow slide. The aminosilane features or patches patterned onto the substrate may serve as landing sites for individual DNA nanoballs, whereas the HMDS may inhibit DNA nanoball landing between features/patches. DNA nanoballs prepared after RCA processes may be loaded into flow slide lanes by pipetting 2- to 3-fold more nanoballs than the number of landing sites available on the slide. Loaded slides may be incubated for 2 h at 23° C. in a closed chamber, and rinsed to neutralize pH and remove unbound DNA nanoballs.

In another embodiment, a few steps may be added to the above described embodiment. First, the silicon wafer may be pretreated so that patterned microwells with desired shape (for example, hollow cylinder) and dimensions may be present on the slide before the growth of silicon oxide layer. Second, when the photoresist surface is exposed with a selected array pattern with a 248 nm lithography tool, the selected array pattern may lead to the ensuing production of discrete regions of exposed HMDS at the bottom of the microwells.

2. Sample Chambers for Bead Emulsion PCR Amplification

Figure 5:
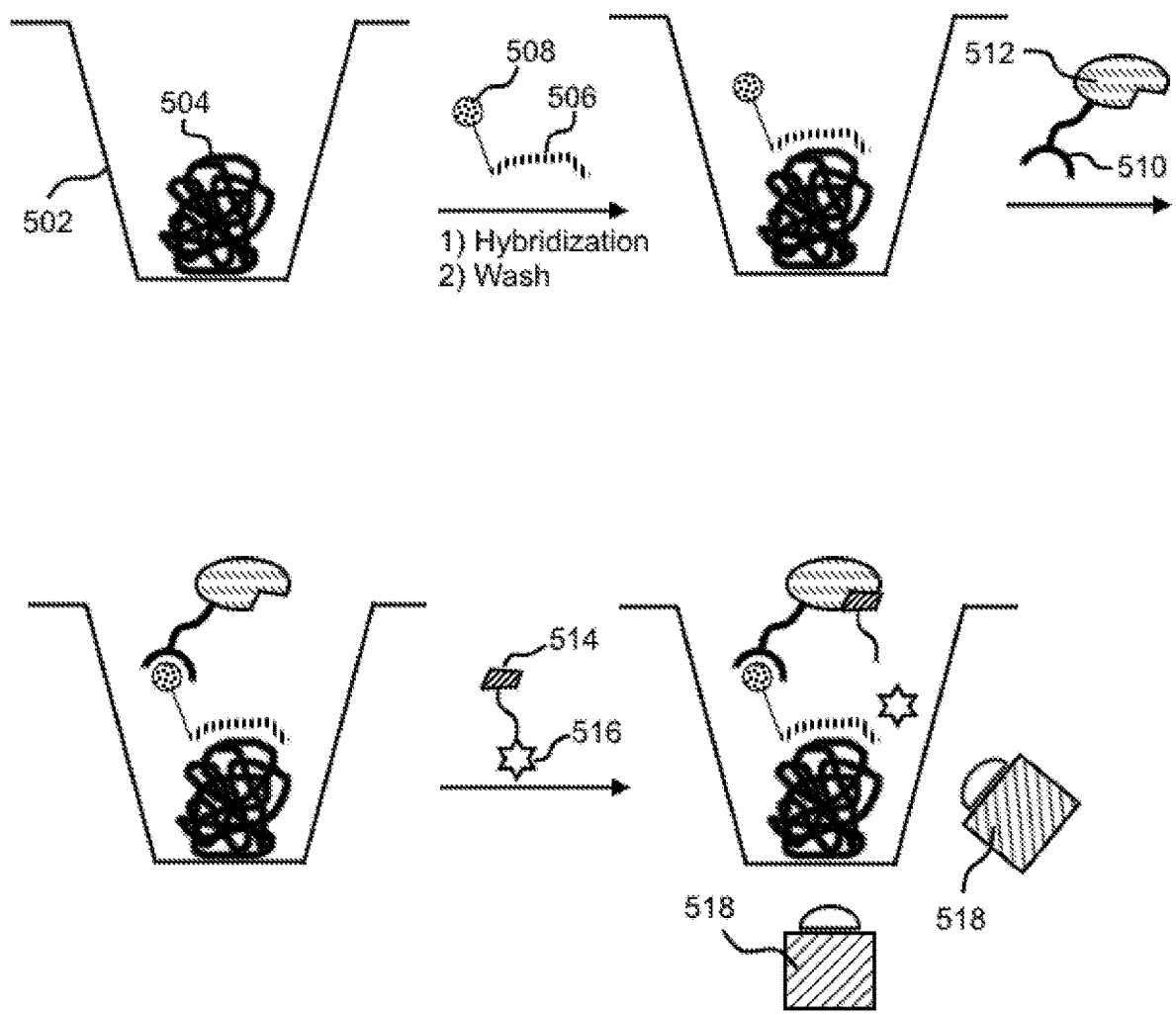
FIG. 5 displays a schematic diagram illustrating the detection of signals indicative of hybridization between the probe and the target nucleic acid according to the present disclosure.

These sample chambers may be produced following procedures similar to those describe above for the sample chambers for nanoballs. However, surface treatment may be different since a microwell with the appropriate dimensions (which allows the attainment of one bead, but does not allow the attainment of two beads) may not undergo surface treatment in order to retain a plurality of copies of a probe. Shown in FIG. 5 is an example of the sample chamber for the bead. Again, the dimensions of the sample chamber may rely on several factors, including 1) the dimensions of the bead each sample chamber retains, 2) the amount of solution allowed in the sample chamber to facilitate the hybridization and washing steps, and 3) the balance between retaining the retained bead and washing away unbound target nucleic acid after the hybridization step, etc.

Decoding of Probe Array

As shown above, the nanoballs or beads with a plurality of copies of probes may be distributed to sample chambers (microwells) randomly. To associate a probe with the sample chamber retaining the probe, the probe sequence retained in each sample chamber may be identified by decoding the coding sequence CS attached to each probe sequence PS. For example, a high-throughput hybridization based decoding procedure, for example, one that is described in Gunderson, et al., "Decoding Randomly Ordered DNA Arrays," *Genome Res.*, 14(5):870-77, 2004, may be used for the decoding purposes. The Gunderson method may provide an algorithm to identify each member of a large collection of barcode-sequence-linked objects through the use of hybridization, and this method can be applied to the manufacture of randomly assembled arrays of beads in wells.

Detection of Hybridization Between the Probe and the Target

As describe above, DNA samples can be fragmented, polished, ligated with adapters in some cases, labeled internally or at 3'-end with biotin or other suitable hapten, including but not limited to, digoxigenin, fluorescein, 2,4-dinitrophenyl (DNP), etc.

As shown in FIG. 5, the probe array may be exposed to the labeled, fragmented target nucleic acid analytes under conditions that allow hybridization between the complementary probe and the fragmented target nucleic acid analyte. A subsequent washing may remove unbound (not hybridized) fragmented target nucleic acid analytes. The washing conditions may be controlled so that the retained beads or nanoballs are not washed away while with unbound nucleic acid analytes are. Detection of the presence of analytes hybridized to probes may be accomplished by many detection methods. The followings are some nonexclusive, illustrative examples:

1. ISFET Detector

In one embodiment, when ISFET detection method is used, the presence of bound target nucleic acid may be detected by exposing the hybridization products to hapten-binding molecules (e.g., streptavidin, anti-digoxigenin, etc.) that is conjugated to a proton signal generating moiety. As described above, the fragmented target nucleic acids are labeled with suitable haptens. As showed in FIG. 5, after a nanoball 504 of a probe is retained in a sample chamber 502, a target nucleic acid 506 and its associated hapten 508 may be allowed to hybridize with the nanoball 504. After the completion of the hybridization step, the hybridized product may be washed at least once to remove unbounded nanoballs and target nucleic acids. Then a hapten-binding molecule 510 and its conjugated proton signal generating moiety 512 may be allowed to react with hapten 508 on the bound target nucleic acid 506 in the sample chamber 502. Then, a substrate 514 which may release at least one proton signal 516 may be added into the sample chamber 502. After the proton signal generating moiety 512 processes the substrate 514, the released proton signal 516 may be detected by a detector 518 which is addressable and adjacent to the sample chamber 502. It can be noted that there may be multiple target nucleic acids bound to the same nanoball of probe within the same sample chamber. This may give a stronger signal than one target nucleic acid binds to the nanoball.

In the present disclosure, the term "proton signal generating moiety" as used herein generally refers to an enzyme that generates acid or base as a byproduct of the catalytic turnover of a substrate or cofactor of the enzyme, thereby causing a measurable pH change in the sample chamber.

Non-exclusive, illustrative examples of proton signal generating moieties include:

Hydrolases such as esterases (e.g., acetylcholinesterase), lipases, phosphatases, and pyrophosphatases (e.g., inorganic pyrophosphatase, ATP hydrolase ("apyrase")), all which produce protons as byproducts due to a biological transformation;

Phosphotransferases such as nucleoside kinase, pyruvate kinase & the like, all of which produce protons as byproducts due to a biological transformation;

Dehydrogenases such as aldehyde dehydrogenase, alcohol dehydrogenase, glucose-t-phosphate dehydrogenase (G6PDH), all of which produce protons as byproducts due to a biological transformation;

Oxidases such as xanthine oxidase, glucose oxidase, and peroxidase, etc., may produce pH changes as well due these enzymes' activities;

Deaminases such as L-glutaminase and urease may produce ammonia ($NH_3$) as a byproduct due to a biological transformation.

In practice, as shown in FIG. 4, after the hybridization and washing step, the proton signal generating moiety conjugated to a hapten-binding molecule may be added to the sample chamber, followed by the addition of the required substrate for the proton signal generating moiety. The resulting pH change, if there is any, may be captured and recorded by the ISFET detector at the associated addressable location.

2. Luminescence Detector

In another embodiment, when luminescence sensor is used, the presence of the bound target nucleic acid that hybridized with a probe may be detected by exposing the probe array to hapten-binding molecules (e.g., streptavidin, anti-digoxigenin, etc.) that may be conjugated to a luminescent signal generating moiety.

A luminescent signal generating moiety can be an enzyme that generates fluorescent or chemiluminescent products from catalytic conversion of a substrate. In one embodiment, an enzyme may convert a substrate to a reaction product that fluoresces when excited by light of a particular wavelength. Non-exclusive, illustrative examples of enzymes capable of producing fluorescent signals include alkaline phosphatase, β-D-galactosidase, and peroxidase in the presence of the appropriate substrate for each enzyme. In another embodiment, an enzyme may convert a substrate to a reaction product that emits photons of light instead of developing a visible color. Non-exclusive, illustrative examples of enzymes capable of producing luminescent signals include alkaline phosphatase, β-D-galactosidase, and peroxidase in the presence of the appropriate substrate for each enzyme.

Computer System

Figure 7:
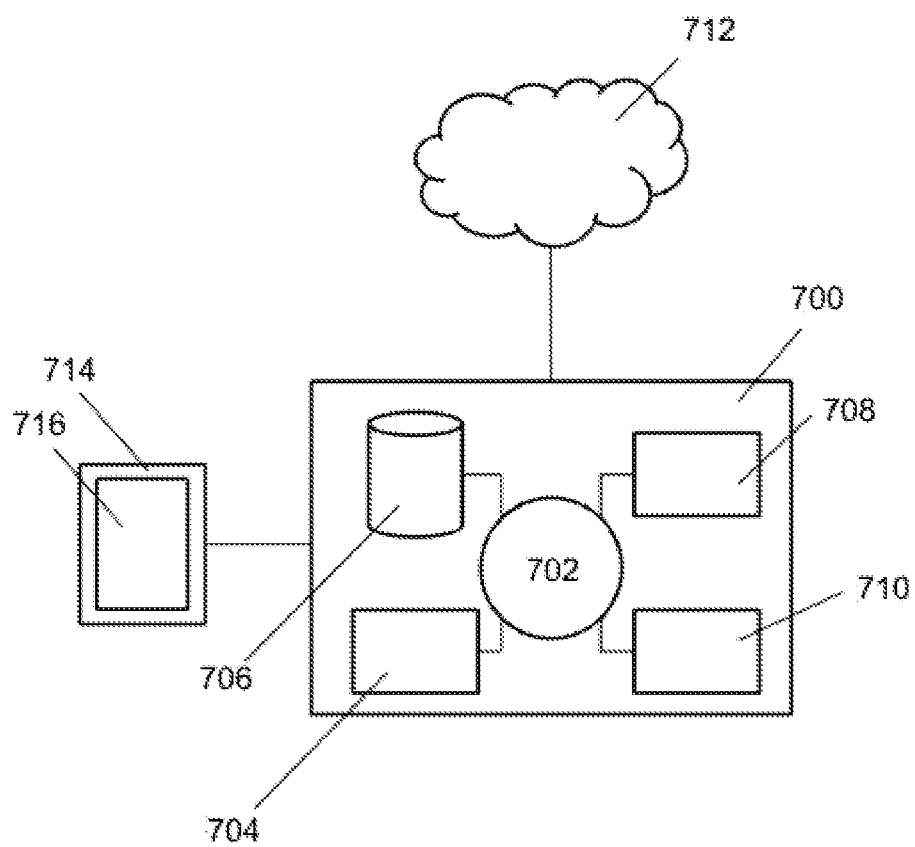
FIG. 7 shows an example schematic of a computer system that is programmed or otherwise configured to implement methods provided herein.

The present disclosure provides computer control system that is programmed to implement methods of the disclosure. FIG. 7 shows a computer system 700 that is programmed or otherwise configured to perform various functions of the methods and systems of the present disclosure, for example, performing an amplification reaction, detecting and/or monitoring the binding of target substances (e.g., target nucleic acids) to an array of probes, and/or monitoring the progress of a hybridization or amplification reaction. The computer system 700 can regulate various aspects of simultaneously performing at least one amplification reaction and detecting changes in signals produced by the probe array, such as, for example, temperature control, reagent handling, and signal detection. The computer system 700 can be intergraded with the systems provided in the present disclosure.

The computer system 700 includes a central processing unit (CPU, also "processor" and "computer processor" herein) 702, which can be a single core or multi core processor, or a plurality of processors for parallel processing. The computer system 700 also includes memory or memory location 704 (e.g., random-access memory, read-only memory, flash memory), electronic storage unit 706 (e.g., hard disk), communication interface 708 (e.g., network adapter) for communicating with one or more other systems, and peripheral devices 710, such as cache, other memory, data storage and/or electronic display adapters. The memory 704, storage unit 706, interface 708 and peripheral devices 710 are in communication with the CPU 702 through a communication bus (solid lines), such as a motherboard. The storage unit 706 can be a data storage unit (or data repository) for storing data. The computer system 700 can be operatively coupled to a computer network ("network") 712 with the aid of the communication interface 708. The network 712 can be the Internet, an internet and/or extranet, or an intranet and/or extranet that is in communication with the Internet. The network 712 in some cases is a telecommunication and/or data network. The network 712 can include one or more computer servers, which can enable distributed computing, such as cloud computing. The network 712, in some cases with the aid of the computer system 700, can implement a peer-to-peer network, which may enable devices coupled to the computer system 700 to behave as a client or a server.

The CPU 702 can execute a sequence of machine-readable instructions, which can be embodied in a program or software. The instructions may be stored in a memory location, such as the memory 704. The instructions can be directed to the CPU 702, which can subsequently program or otherwise configure the CPU 702 to implement methods of the present disclosure. Examples of operations performed by the CPU 702 can include fetch, decode, execute, and writeback.

The CPU 702 can be part of a circuit, such as an integrated circuit. One or more other components of the system 700 can be included in the circuit. In some cases, the circuit is an application specific integrated circuit (ASIC).

The storage unit 706 can store files, such as drivers, libraries and saved programs. The storage unit 706 can store user data, e.g., user preferences and user programs. The computer system 700 in some cases can include one or more additional data storage units that are external to the computer system 700, such as located on a remote server that is in communication with the computer system 700 through an intranet or the Internet.

The computer system 700 can communicate with one or more remote computer systems through the network 712. For instance, the computer system 700 can communicate with a remote computer system of a user (e.g., a lab technician, a physician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 700 via the network 712.

Methods as described herein can be implemented by way of machine (e.g., computer processor) executable code stored on an electronic storage location of the computer system 700, such as, for example, on the memory 704 or electronic storage unit 706. The machine executable or machine readable code can be provided in the form of software. During use, the code can be executed by the processor 702. In some cases, the code can be retrieved from the storage unit 706 and stored on the memory 704 for ready access by the processor 1905. In some situations, the electronic storage unit 706 can be precluded, and machine-executable instructions are stored on memory 704.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 700, can be embodied in programming. Various aspects of the technology may be thought of as "products" or "articles of manufacture" in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 700 can include or be in communication with an electronic display 714 that comprises a user interface (UI) 716 for providing, for example, cycle numbers, temperature values, temperature control, detector data, and reagent handling. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 702. The algorithm can, for example, control the temperatures of each of the addressable locations, assign barcode of the probe to each of the addressable locations, collect signals and analyze collected data.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for assaying a presence of a target nucleic acid in a sample, comprising:
   (a) providing a chip comprising a sensor adjacent to a sample chamber, wherein the sample chamber retains a plurality of copies of a capture probe, wherein the capture probe is part of a library of a plurality of capture probes, wherein the plurality of copies of the capture probe are not attached to a surface of the sample chamber, directly or indirectly, via a covalent bond,
   wherein the capture probe comprises:
   1) a sequence of a nucleic acid fragment that is complementary to at least a portion of the target nucleic acid; and
   2) a barcode sequence attached to a first end of the sequence of the nucleic acid fragment in 1);
   (b) providing a sample in the sample chamber under conditions that permit the capture probe to selectively couple to a target nucleic acid in the sample, wherein the capture probe selectively couples to the target nucleic acid;
   (c) detecting, by the sensor, at least one signal indicative of a presence or absence of the target nucleic acid in the sample chamber; and (d) determining the presence or absence of the target nucleic acid in the sample.

2. The method of claim 1, wherein the sensor is in an array of a plurality of sensors in the chip, wherein the sample chamber is in an array of a plurality of sample chambers in the chip, and wherein each of the plurality of sample chambers is adjacent to at least one sensor of the array of the plurality of sensors.

3. The method of claim 1, wherein the target nucleic acid is a fragment of a first nucleic acid.

4. The method of claim 1, further comprising prior to (a):
(a1) circularizing an adaptor-coupled capture probe template; and
(a2) amplifying the adaptor-coupled capture probe template to form a linear amplified concatamer molecule comprising a plurality of copies of the capture probe.

5. The method of claim 1, wherein the barcode sequence is between 3 and 30 nucleotides in length.

6. The method of claim 1, further comprising prior to (a):
(a1) delivering a single copy of a template for the capture probe or a single copy of a double-stranded nucleic acid comprising the capture probe into an aqueous microreactor in a water-in-oil emulsion, wherein the microreactor comprises a plurality of a primer capable of annealing to the capture probe, a single bead capable of binding to the template of the capture probe and amplifying a first copy of the capture probe which becomes attached to the bead, and an amplification reaction solution containing reagents necessary to perform nucleic acid amplification;
(a2) subjecting the microreactor to a nucleic acid amplification reaction under conditions that yield the first copy of the capture probe;
(a3) repeating step (a2) multiple times; and
(a4) breaking the water-in-oil emulsion and producing multiple copies of the capture probe attached to the bead.

7. The method of claim 1, wherein the sample comprises a plurality of target nucleic acid molecules, including the target nucleic acid.

8. The method of claim 7, wherein the sensor is part of an array of a plurality of sensors, wherein each of the plurality of sensors detects the presence or absence of at least one of the plurality of target nucleic acid molecules, and wherein each sensor of the array of the plurality of sensors is individually addressable.

9. The method of claim 8, wherein each capture probe comprises:
1) a sequence of a nucleic acid fragment that is complementary to a portion of one of the target nucleic acids; and
2) a barcode sequence attached to a first end of the sequence of the nucleic acid fragment;

and wherein (d) comprises:
(d1) decoding the barcode sequence of the capture probe retained at the corresponding sample chamber associated with the individually addressable sensor.

10. The method of claim 1, wherein the chip comprises an additional sensor, wherein the sample comprises the target nucleic acid and an additional target nucleic acid, and wherein the additional sensor detects the additional target nucleic acid.

11. The method of claim 10, wherein the additional sensor is adjacent to an additional sample chamber, wherein the additional sample chamber is configured to retain a plurality of copies of an additional capture probe, wherein the additional capture probe selectively couples to the additional target nucleic acid.

12. The method of claim 1, wherein the sensor comprises an ion-sensitive field effect transistor (ISFET).

13. The method of claim 1, wherein the sensor comprises a chemically-sensitive field effect transistor (chemFET).

14. The method of claim 1, wherein the at least one signal comprises a change of pH.

15. A system for assaying a presence of a target nucleic acid in a sample, comprising:
(a) a chip comprising a sensor adjacent to a sample chamber, wherein the sample chamber is configured to retain the sample having the target nucleic acid and a plurality of copies of a capture probe, wherein the capture probe selectively couples to the target nucleic acid, wherein the plurality of copies of the capture probe are not attached to a surface of the sample chamber via a covalent bond, and wherein the sensor detects at least one signal from the sample, which at least one signal is indicative of a presence or absence of the target nucleic acid;
(b) a computer processor coupled to said chip and programmed to (i) measure the at least one signal while subjecting the chip in contact with the sample; and (ii) determine the presence or absence of the target nucleic acid in the sample.

16. The system of claim 15, wherein the sensor is in an array of a plurality of sensors in the chip, wherein the sample chamber is in an array of a plurality of sample chambers in the chip, wherein each of the plurality of sample chambers is adjacent to at least one sensor of the array of the plurality of sensors, and wherein each sensor is individually addressable.

17. The system of claim 16, wherein the computer processor is further programmed to (iii) map the array of individually addressable sensors; and (iv) when the capture probe contains a barcode sequence, to associate the barcode sequence with the corresponding individually addressable sensor.

18. The system of claim 15, wherein the sensor is ion-sensitive filed effect transistor (ISFET), chemically-sensitive filed effect transistor (chemFET), or optical sensor.

* * * * *